(12) United States Patent
Fagot et al.

(10) Patent No.: US 6,184,252 B1
(45) Date of Patent: *Feb. 6, 2001

(54) 2-AMINO-1,3-ALKANEDIOL COMPOSITIONS FOR INDUCING/STIMULATING HAIR GROWTH AND/OR RETARDING HAIR LOSS

(75) Inventors: Dominique Fagot; Olivier Gaillard, both of Paris; Michel Philippe, Wissous; Bruno Bernard, Neuilly sur Seine, all of (FR)

(73) Assignee: Societe L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/801,315

(22) Filed: Feb. 18, 1997

(30) Foreign Application Priority Data

Feb. 15, 1996 (FR) .................................................. 96 01886

(51) Int. Cl.[7] ...................................................... A61K 31/16
(52) U.S. Cl. .......................... 514/625; 514/627; 514/629; 514/549; 514/551; 514/880
(58) Field of Search ..................................... 514/549, 551, 514/669, 625, 627, 629

(56) References Cited

FOREIGN PATENT DOCUMENTS

| 0278505 | 8/1988 | (EP) . |
|---|---|---|
| 2718960 | 10/1995 | (FR) . |
| 63-255213 | * 10/1988 | (JP) . |
| 92/16236 | 10/1992 | (WO) . |
| 94/23694 | 10/1994 | (WO) . |
| 95/03028 | 2/1995 | (WO) . |

OTHER PUBLICATIONS

CA 118: 219470, Dubief et al., Feb. 18, 1993.*
CA 116: 180920, Iwao et al, Jan. 9, 1992.*
CA 114: 149919, Guy et al., Oct. 24, 1990.*
CA 126: 79954, Weder et al., Nov. 28, 1996.*
CA 125: 308691, Philippe et al., Oct. 9, 1996.*
CA 125: 284338, Saint–Leger et al., Aug. 28, 1996.*
CA 125: 284358, Greff et al., Jul. 12, 1996.*
CA 125: 95551, Pillai et al., May 15, 1996.*
CA 125: 18664, Launet–Martin et al., Apr. 3, 1996.*
CA 124: 269967, Braida et al., Mar. 6, 1996.*
CA 123: 349840, Philippe et al., 1995.*
Patent Abstracts of Japan, vol. 13, No. 63 (C–568) [3411] 1989.
Patent Abstracts of Japan, vol. 13, No. 49 (C–565) [3397] 1989.

* cited by examiner

*Primary Examiner*—Rebecca Cook
(74) *Attorney, Agent, or Firm*—Burns, Doane, Swecker & Mathis, L.L.P.

(57) ABSTRACT

Topically applicable hair growth-/hair loss-affecting cosmetic/pharmaceutical compositions for treating mammalian subjects with hair or scalp disorders, comprise an effective amount of at least one 2-amino-1,3-alkanediol compound having the structural formula (I):

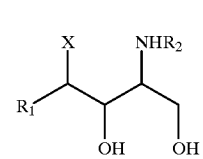

formulated into a physiologically topically acceptable carrier medium therefor.

21 Claims, No Drawings

2-AMINO-1,3-ALKANEDIOL COMPOSITIONS FOR INDUCING/STIMULATING HAIR GROWTH AND/OR RETARDING HAIR LOSS

BACKGROUND OF THE INVENTION

1. Technical Field of the Invention

The present invention relates to novel cosmetic and/or pharmaceutical compositions for topical application to the hair and/or scalp of mammalian subjects, comprising an effective amount of at least one 2-amino-1,3-alkanediol, or derivative thereof, and to the use of such novel compositions for inducing and/or stimulating hair growth and/or retarding hair loss.

2. Description of the Prior Art

In human subjects, hair growth and its renewal are principally determined by the activity of the hair follicles. This activity is cyclical and essentially entails three phases, namely, the anagenic phase, the catagenic phase and the telogenic phase.

The active anagenic phase, or growth phase, which lasts for several years and during which the hair grows longer, is followed by a very short and transitory catagenic phase, which lasts a few weeks, and then by a resting or quiescent phase, designated the telogenic phase, which lasts a few months.

At the end of the rest period, the hair falls out and another cycle begins anew. The head of hair is thus constantly renewed and, of the approximately 150,000 hairs on a human head, at any given instant approximately 10% are at rest and will therefore be replaced in a few months.

In a significant number of cases, early hair loss occurs in genetically predisposed subjects and it affects men in particular. It is more particularly androgenetic or androgenic alopecia or, alternatively, androgeno-genetic alopecia.

This alopecia is essentially due to a disturbance in hair renewal which results, at first, in an acceleration in the frequency of the cycles at the expense of the quality of the hair and then of its amount. A progressive thinning of the head of hair occurs by regression of the so-called "terminal" hairs to the downy stage. Certain regions are preferentially affected, in particular the temple or frontal areas in men and, in women, a diffuse alopecia of the vertex is observed.

Compositions that eliminate or reduce the effects of alopecia and, in particular, that induce or stimulate hair growth or decrease hair loss have long been considered desiderata in the cosmetic and pharmaceutical industries.

In this regard, a large number of very diverse active compounds or substances have already been suggested for such purposes, for example vitamins, such as vitamin E, amino acids, such as serine or methionine, vasodilators, such as acetylcholine and derivatives thereof, female hormones, such as estradiol, keratolytic agents, such as salicylic acid, or chemical compounds, such as 2,4-diamino-6-piperidinopyrimidine 3-oxide or "Minoxidil," described in U.S. Pat. No. 4,596,812 or, alternatively, its many derivatives, such as those described in EP-353,123, EP-356,271, EP-408,442, EP-522,964, EP-420,707, EP-459,890 and EP-519,819.

Also exemplary thereof are 6-amino-1,2-dihydro-1-hydroxy-2-imino-4-piperidinopyrimidine and derivatives thereof, which are described, more particularly, in U.S. Pat. No. 4,139,619.

Nonetheless, considerable research and development is continuing in this art in quest of yet other such valuable active agents.

Minoxidil, while it remains the reference compound in the field, exhibits not insignificant side effects which complicate the use thereof.

SUMMARY OF THE INVENTION

Accordingly, a major object of the present invention is the provision of compounds of the 2-amino-1,3-alkanediol type for efficaciously inducing/stimulating hair growth and/or decreasing hair loss, without exhibiting the disadvantages and drawbacks to date characterizing the state of this art.

DETAILED DESCRIPTION OF BEST MODE AND SPECIFIC/PREFERRED EMBODIMENTS OF THE INVENTION

More particularly according to the present invention, the 2-amino-1,3-alkanediol type compounds or derivatives thereof constitute active agents emanating from tissues which are known to the art by the very general term of "sphingolipids."

Among these sphingolipids, N-acylated derivatives based on sphinganine [(2S,3R)-2-amino-1,3-octadecanediol] are ceramides mostly present in the hair, whereas the analogous derivatives based on sphingenine [(2S,3R,4E)-2-amino-4-octadecene-1,3-diol), other ceramides, constitute a fraction of the lipids mostly present in the stratum corneum of the skin.

The ceramides are formulated into cosmetics in the natural or synthetic state, for example, to reinforce the barrier effect of the stratum corneum in order to reduce water loss and thus dryness of the skin (GB-2,178,312, GE-2,213,723, EP-227,994, EP-282,616 and EP-556,957).

They are also formulated into cosmetic compositions for their properties which confer a better elasticity on the skin (EP-500,437) or into compositions for hair use in order to reinforce the hair and/or to repair the damage caused by the continual attacks to which the latter is subjected.

Hitherto, to the knowledge of the assignee hereof, it has never been described nor even suggested that 2-amino-1,3-alkanediols or derivatives thereof exert an effect or influence on cell proliferation and still less on keratinocyte proliferation.

It is on the basis of this new property of these aminodiols that it has unexpectedly been shown that these compounds also exert an effect on the survival of the hair follicle.

Thus, by increasing the survival time of the hair follicle, the anagenic phase of the hair cycle is lengthened, which has the effect of delaying hair loss.

Among the sphingolipids, compounds based on sphingenine induce apoptosis, directly or through a series of events involving cellular proteins. This phenomenon, which results in cell death, transposed to the hair cycle, elicits a halt in the growth of the follicle and in hair loss.

The synthesis of compounds based on sphingenine results from several distinct mechanisms. Exemplary are the activation of cellular sphingomyelinase by α-type tumor necrosis factor (TNF-α), by vitamin D, by interleukin-1, by the FAS antigen or ionizing radiation. It is also known that compounds based on sphingenine can also be generated by activation of acyl-CoA: sphinganine (sphingosine) N-acyltransferase (EC 2.3.1.24).

Thus, it has now unexpectedly been determined that the compounds of formula (I) can interfere both during the synthesis of the compounds based on sphingenine and during the events induced by these compounds. The consequence of this is to prevent the apoptosis induced by the compounds based on sphingenine and also to stimulate cell growth and viability.

In chemotherapeutic anticancer treatments, the use of anticancer agents causes cell death in the hair follicle, resulting in hair loss. This induced alopecia is generally transitory, but can sometimes be permanent (A. M. Hussein, *South Med. J.*, 1993, 86, 489–496). This side effect causes some patients to refuse this type of therapy (K. O. Baxley et al., *Cancer Nurs.*, 1984, 7, 499–503).

Doxorubicin, for example, induces such a hair loss. It is known that doxorubicin activates ceramide synthase, an enzyme whose activation results in an increase in the intracellular level of compounds based on sphingenine which themselves induce the phenomenon of apoptosis and of cell death.

It has now been determined that the compounds of formula (I) below counteract the harmful side effects of anticancer agents, such as, for example, doxorubicin, by increasing the cell viability of the keratinocytes of the hair follicles.

The present invention features the formulation, into cosmetic/pharmaceutical compositions, as active agents promoting hair survival and/or growth, of at least one compound having the general formula (I):

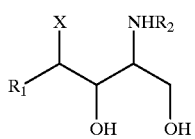

(I)

in which $R_1$ is a saturated or unsaturated, optionally hydroxylated, linear or branched hydrocarbon radical having from 4 to 28 carbon atoms; $R_2$ is a hydrogen atom or the radical:

wherein $R_3$ is a saturated or unsaturated, optionally hydroxylated, linear or branched hydrocarbon radical having from 1 to 29 carbon atoms, with the proviso that the hydroxyl group thereof may be esterified by a saturated or unsaturated, linear or branched acyl radical having from 2 to 30 carbon atoms; and X is a hydrogen atom or the OH radical, or of at least one of its optical isomers or one of the diastereoisomers.

$R_1$ preferably has from 11 to 23 carbon atoms and even more preferably 14 carbon atoms.

$R_2$ preferably is the radical:

wherein $R_3$ preferably has from 7 to 25 carbon atoms.

$R_1$ is preferably a saturated and/or linear hydrocarbon radical, more particularly a saturated linear hydrocarbon radical.

$R_1$ is more preferably a saturated hydrocarbon radical having 14 carbon atoms and even more preferably $R_1$ is a saturated linear hydrocarbon radical having 14 carbon atoms.

The active agent promoting hair survival and/or growth can be a mixture of compounds of formula (I) for which $R_1$ and/or $R_2$ are radicals of different chain lengths.

These compounds can be employed in the form of a pure isomer or of a mixture of isomers.

These compounds present the advantage of not inducing undesirable side effects, which makes their use without risk for the user.

Exemplary compounds of formula (I) include:
2-Amino-1,3-octadecanediol;
2-Acetylamino-1,3-octadecanediol;
2-Octanoylamino-1,3-octadecanediol;
2-Tetracosanoylamino-1,3-octadecanediol;
2-N-(2-Hydroxyhexadecanoyl)amino-1,3-octadecanediol;
2-Oleoylamino-1,3-octadecanediol;
2-Hexadecanoylamino-1,3-octadecanediol;
2-N-(2-Hydroxydocosanoyl)amino-1,3-octadecanediol;
2-Amino-1,3,4-octadecanetriol;
2-Hexadecanoylamino-1,3,4-octadecanetriol; and
2-N-(2-Hydroxyhexadecanoyl)amino-1,3,4-octadecanetriol.

In a preferred embodiment according to the invention, 2-N-(2-hydroxyhexadecanoyl)amino-1,3-octadecanediol and 2-oleoylamino-1,3-octadecanediol are employed.

The amount of the compounds of formula (I) which are advantageously used according to the invention depends, of course, on the nature of the compound itself, on its physicochemical properties and on the technique for the application thereof. One skilled in this art is cognizant how to adjust the amount of the at least one compound of formula (I) according to the requirements thereof.

For example, the compounds of formula (I) can be formulated at concentrations by weight of from $10^{-4}\%$ to 20% and preferably from $10^{-3}\%$ to 10% in the composition.

The present invention also features the use of at least one compound of formula (I) for combating an alopecia induced by an anticancer treatment entailing chemotherapy.

When the compound of formula (I) is formulated into a composition which must be topically applied onto the skin and particularly onto the scalp, this composition can be provided in all of the pharmaceutical dosage forms typically employed.

For topical application onto the skin, the composition can be in the form, in particular, of an aqueous, alcoholic, aqueous/alcoholic or oily solution, or of a dispersion of the lotion or serum type, of an emulsion having a liquid or semi-liquid consistency of the milk type, obtained by dispersion of a fatty phase in an aqueous phase (O/W) or vice versa (W/O), or of a suspension or of an emulsion with a soft consistency of the aqueous or anhydrous gel, foam or cream type, or, alternatively, of microcapsules or microparticles, or of a vesicular dispersion of ionic and/or nonionic type. It can also be in the form of an aerosol composition also comprising a pressurized propellant agent.

Whatever its form, this composition is formulated according to the usual techniques.

The amounts of the different constituents of the compositions according to the invention are those that are conventional in the fields under consideration.

The compounds according to the invention can also be formulated into various compositions for hair care and, in particular, shampoos, hair-setting lotions, treating lotions, styling creams or gels, dye compositions (in particular oxidation dyes), optionally in the form of color-enhancing shampoos, hair-restructuring lotions, permanent-wave compositions (in particular compositions for the first step of a permanent wave), shampoos for combating parasites, and the like.

When the subject composition comprises an emulsion, the proportion of the fatty phase advantageously ranges from 5% to 80% by weight, and preferably from 5% to 50% by weight, with respect to the total weight of the composition. The oils, the waxes, the emulsifiers and the coemulsifiers comprising the composition in the emulsion form are selected from among those conventionally used in the cosmetics field. The emulsifier and the coemulsifier are present, in the composition, in a proportion advantageously ranging from 0.3% to 30% by weight, and preferably from 0.5% to 20% by weight, with respect to the total weight of the composition. The emulsion can, in addition, contain lipid vesicles.

When the composition is an oily gel or solution, the fatty phase can constitute more than 90% of the total weight of the composition.

Also intended are compositions comprising at least one compound of formula (I) as an active principle intended to induce and/or to stimulate hair growth and/or to slow down or retard its loss comprising liposomed form, such as, in particular, described in WO-94/22468, filed Oct. 13, 1994 and assigned to Anti-Cancer Inc. The compound encapsulated in the liposomes can thus be delivered selectively to the hair follicle.

The subject compositions can also contain additives and adjuvants which are conventional in the cosmetics field, such as hydrophilic or lipophilic gelling agents, hydrophilic or lipophilic additives, preservatives, antioxidants, solvents, fragrances, fillers, screening agents, odor absorbers and colorants. The amounts of these different additives and adjuvants are those typically employed in the cosmetics field and range, for example, from 0.01% to 10% of the total weight of the composition. These additives and adjuvants, depending on the nature thereof, can be introduced into the fatty phase, into the aqueous phase and/or into the lipid spherules.

Exemplary oils or waxes according to the invention include mineral oils (liquid petrolatum), vegetable oils (liquid fraction of karite butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. Fatty alcohols and fatty acids (stearic acid) can be added to these oils.

Exemplary emulsifiers which are suitable per the invention include glyceryl stearate, polysorbate 60 and the PEG-6/PEG-32/glycol stearate mixture marketed under the trademark Tefose®63 by Gattefosse.

Exemplary solvents according to the invention include the lower alcohols, in particular ethanol and isopropanol, or propylene glycol.

And exemplary hydrophilic gelling agents include carboxyvinyl polymers (carbomer), acrylic copolymers such as acrylate/alkyl acrylate copolymers, polyacrylamides, polysaccharides such as hydroxypropylcellulose, natural gums and clays and representative lipophilic gelling agents include the modified clays such as bentones, metal salts of fatty acids such as aluminum stearates, and hydrophobic silica, ethylcellulose or polyethylene.

The subject compositions can also contain other hydrophilic active principles, such as proteins or protein hydrolysates, amino acids, polyols, urea, allantoin, sugars and sugar derivatives, water-soluble vitamins, plant extracts and hydroxy acids.

Exemplary such lipophilic active principles include those of retinol (vitamin A) and derivatives thereof, tocopherol (vitamin E) and derivatives thereof, essential fatty acids, ceramides other than the compounds of formula (I), essential oils or salicylic acid and derivatives thereof.

It is also envisaged to formulate, in combination with the compounds of formula (I), compounds which further improve the activity with respect to hair regrowth and/or with respect to slowing down or retarding hair loss and which are already known to this art for such activity.

Exemplary such compounds include, without limitation:
(a) nicotinic acid esters, including in particular tocopherol nicotinate, benzyl nicotinate and $C_1$–$C_6$ alkyl nicotinates, such as methyl nicotinate or hexyl nicotinate;
(b) pyrimidine derivatives, such as 2,4-diamino-6-piperidinopyrimidine 3-oxide or "Minoxidil," described in U.S. Pat. No. 4,596,812 or, alternatively, its many derivatives, or compounds such as 6-amino-1,2-dihydro-1-hydroxy-2-imino-4-piperidinopyrimidine and derivatives thereof, as described in U.S. Pat. No. 4,139,619;
(c) agents promoting hair regrowth, such as those described in published European patent application No. 0,648,488 assigned to the assignee hereof;
(d) antibacterial agents, such as macrolides, pyranosides and tetracyclines, and in particular erythromycin;
(e) calcium antagonists, such as cinnarizine and diltiazem;
(f) hormones, such as estriol or analogs thereof, or thyroxine and its salts;
(g) steroidal anti-inflammatory agents, such as corticosteroids (for example hydrocortisone);
(h) antiandrogen agents, such as oxendolone, spironolactone or diethylstilbestrol;
(i) 5-α-reductase antagonists;
(j) OH-radical scavengers, such as dimethyl sulfoxide.

Other such compounds include, for example, diazoxide, spiroxazone, phospholipids, such as lecithin, linoleic and linolenic acids, salicylic acid and derivatives described in FR-2,581,542, such as the derivatives of salicylic acid bearing an alkanoyl substituent having from 2 to 12 carbon atoms in the 5 position of the benzene ring, hydroxycarboxylic or ketocarboxylic acids and esters thereof, lactones and their corresponding salts, anthralin, carotenoids, eicosatetraenoic and eicosatrienoic acids or the esters and amides thereof, or vitamin D and derivatives thereof.

According to the invention, it is possible, inter alia, to combine at least one compound of formula (I) with other active agents intended, in particular, for the prevention and/or the treatment of cutaneous conditions, particularly conditions of the scalp. Exemplary of such active agents are:
(1) agents which modulate cutaneous pigmentation and/or proliferation and/or differentiation, such as retinoic acid and its isomers, retinol and its esters, vitamin D and its derivatives, estrogens, such as estradiol, kojic acid or hydroquinone;
(2) antibacterials, such as clindamycin phosphate, erythromycin or antibiotics from the tetracycline class;
(3) agents for combating parasites, in particular metronidazole, crotamiton or pyrethroids;
(4) antifungals, in particular compounds belonging to the imidazole class, such as econazole, ketoconazole or miconazole or their salts, polyene compounds, such as amphotericin B, compounds of the allylamine family, such as terbinafine, or alternatively octopirox;
(5) antiviral agents, such as acyclovir;
(6) steroidal anti-inflammatory agents, such as hydrocortisone, betamethasone valerate or clobetasol propionate, or nonsteroidal anti-inflammatory agents, such as ibuprofen and its salts, diclofenac and its salts, acetylsalicylic acid, acetaminophen or glycyrrhetinic acid;

(7) anaesthetic agents, such as lidocaine hydrochloride and derivatives thereof;

(8) antipruriginous agents, such as thenaldine, trimeprazine or cyproheptadine;

(9) keratolytic agents, such as α- and β-hydroxycarboxylic acids or β-ketocarboxylic acids, their salts, amides or esters and more particularly hydroxy acids, such as glycolic acid, lactic acid, salicylic acid, citric acid and, generally, fruit acids, and 5-(n-octanoyl)salicylic acid;

(10) agents for combating free radicals, such as α-tocopherol or its esters, superoxide dismutases, certain metal chelating agents or ascorbic acid and its esters;

(11) antiseborrhoeics, such as progesterone;

(12) antidandruff agents, such as octopirox or zinc pyrithione;

(13) antiacne agents, such as retinoic acid or benzoyl peroxide;

(14) substances such as substance P, CGRP or bradykinin antagonists or NO synthase inhibitors, which compounds are described as being active for the treatment of sensitive skins and as exhibiting antiirritant effects, in particular with respect to irritant compounds possibly present in the compositions.

Thus, this invention also features compositions comprising an effective amount of at least one compound of formula (I) and at least one active agent selected from among antibacterial agents, agents for combating parasites, antifungal agents, antiviral agents, anti-inflammatory agents, antipruriginous agents, anaesthetic agents, keratolytic agents, agents for combating free radicals, antiseborrhoeic agents, antidandruff agents, antiacne agents, agents which modulate cutaneous pigmentation and/or proliferation and/or differentiation, substance P, CGRP (calcitonin gene related peptide) or bradykinin antagonists or NO synthase inhibitors.

In the compositions according to the invention, the substance P, CGRP or bradykinin antagonist or the NO synthase inhibitor is preferably incorporated in an amount ranging from 0.000001% to 20% of the total weight of the composition and in particular in an amount constituting from 0.0001% to 15% of the total weight of the composition.

It is envisaged to employ at least one of the compounds corresponding to the formula (I) for the formulation of a pharmaceutical, particularly dermatological, composition intended to treat hair loss and/or to promote hair regrowth.

In general, these pharmaceutical compositions are distinguished, in particular, from cosmetic compositions by the amount of active principle which they contain. One skilled in this art can readily determine the amount of active principle which can be used as a function of the result desired, but also taking account of the mode of administration envisaged.

For example, the compound of formula (I) can be employed for the preparation of a pharmaceutical composition at a concentration of from 0.01% to 20% and preferably from 0.1% to 10% by weight with respect to the weight of the composition.

The cosmetic or pharmaceutical compositions according to the invention can be topically applied onto the alopecic areas of the scalp and hair of an individual and optionally maintained in contact for a number of hours and optionally rinsed. It is possible, for example, to apply the composition containing an effective amount of at least one compound of formula (I) in the evening, to retain the composition in contact overnight and optionally to shampoo in the morning. These applications can be repeated daily for one or a number of months, depending on the particular individuals involved.

Thus, the present invention also features a regimen for the cosmetic treatment of the hair and/or of the scalp, comprising topically applying onto the hair and/or the scalp, a cosmetic composition comprising an effective amount of at least one compound of formula (I) in a physiologically topically acceptable carrier medium therefor, maintaining this composition in contact with the hair and/or the scalp, and optionally later rinsing the same therefrom.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Measurement of the Proliferative Influence of 2-amino-1,3-octadecanediol and Derivatives Thereof on Cultured Keratinocytes HaCat cells (Boukamp and coworkers, *J. Cell Biol.*, vol. 106, March 1988, 761–771) were cultured in DMEM medium (marketed by Gibco) containing amino acids (mixture of nonessential amino acids) at a concentration of 0.1 mM, penicillin and streptomycin at respective concentrations of 50 International Units per millimeter and of 50 μg/ml, glutamine at a concentration of 2 mM, sodium pyruvate at a concentration of 1 mM and 10% fetal calf serum. These cells were inoculated at a density of 10,000 cells per well in the 24 wells of plates of the multiwell type (Costar, France). 24 hours after inoculation, the cells were contacted with the various test compounds in a KBM medium (marketed by Clonetics) containing 0.15 mM of calcium ion, insulin at 5 μg/ml, hydrocortisone at 0.5 μg/ml and lipid-free bovine serum albumin at 1 μg/ml.

Cellular counting was carried out 5 days after the addition of the various ceramides using a cell counter of the Coulter Counter type.

The various compounds were tested at 0.5 nM, 5 nM, 50 nM and 500 nM.

The results, expressed as percentage, represent the increase in the number of cells with respect to the control, namely, with respect to a culture produced under the same conditions in the absence of sphinganine.

The different compounds tested were:

A: 2-amino-1,3-octadecanediol,

B: 2-oleoylamino-1,3-octadecanediol,

C: 2-N-(2-hydroxyhexadecanoyl)amino-1,3-octadecanediol,

D: 2-tetracosanoylamino-1,3-octadecanediol,

E: 2-acetylamino-1,3-octadecanediol,

F: 2-octanoylamino-1,3-octadecanediol.

|        | A  | B  | C  | D  | E  | F  |
|--------|----|----|----|----|----|----|
| 0.5 nM | 7  | 17 | 26 | 22 | 17 | 15 |
| 5 nM   | 15 | 24 | 36 | 27 | 34 | 18 |
| 50 nM  | 17 | 23 | 42 | 33 | 29 | 31 |
| 500 nM | 30 | 14 | 22 | 42 | 35 | 27 |

These results evidence that 2-amino-1,3-octadecanediol and derivatives thereof exhibit a proliferative activity with respect to cultured keratinocytes.

EXAMPLE 2

Measurement of the Effect of 2-amino-1,3-octadecanediol and Derivatives Thereof on Cell Viability HaCat cells were cultured as in Example 1.

These were then inoculated at a density of 20,000 cells per well in the 24 wells of plates of the multiwell type (Costar, France).

24 hours after inoculation, the cells were contacted with the various test compounds in a KBM medium (marketed by Clonetics) containing insulin at 5 µg/ml and hydrocortisone at 0.5 µg/ml.

Cell viability was evaluated 48 hours later by measuring the mitochondrial respiration. This was carried out using an XTT kit, marketed by Boehringer, according to the supplier's instructions.

The compounds A, B and C of the above Example 1 were tested at a concentration of 50 nM, as well as a derivative based on sphingenine: N-palmitoylsphingenine marketeed by Sigma (C16H).

The results, expressed as percentage, represent the increase in the number of cells with respect to the control, namely, with respect to a culture produced under the same conditions in the absence of alkanediol compounds.

| Control | 0   |
|---------|-----|
| A       | +17 |
| B       | +23 |
| C       | +20 |
| C16H    | −25 |

The results evidence that 2-amino-1,3-octadecanediol (A), 2-oleoylamino-1,3-octadecanediol (B) and 2-N-(2-hydroxyhexadecanoyl)amino-1,3-octadecanediol (C) increased the viability of the cultured keratinocytes, whereas N-palmitoylsphingenine (C16H) elicited a cytotoxic effect on the cultured cells.

This result indicates that compounds based on sphingenine cannot be used for the treatment of hair follicles since they cause cell death in culture.

EXAMPLE 3

Measurement of the Effect of 2-amino-1,3-octadecanediol and Derivatives Thereof on the Cell Cycle HaCat cells were cultured as above.

These were then inoculated at a density of 20,000 cells per well in the 24 wells of plates of the multiwell type (Costar, France).

24 hours after inoculation, the cells were contacted with the various test compounds in a KBM medium (marketed by Clonetics) containing insulin at 5 µg/ml and hydrocortisone at 0.5 µg/ml and 5-bromo-2'-deoxyuridine (BrdU) at 1 µM.

The phase of the cell cycle was evaluated 48 hours later by measuring the incorporation of BrdU in genomic deoxyribonucleic acid. This was carried out using a BrdU fast kit, marketed by Boehringer, according to the supplier's instructions.

The compounds A, B and C of the above example were tested at a concentration of 50 nM.

The results, expressed as percentage, represent the increase in the number of cells which have entered into the S phase with respect to the control, namely, with respect to a culture produced under the same conditions in the absence of alkanediol compounds.

|         | 72 hours | 96 hours |
|---------|----------|----------|
| Control | 0        | 0        |
| A       | 36       | 41       |
| B       | 43       | 51       |
| C       | 17       | 43       |

The results evidence that 2-amino-1,3-octadecanediol (A), 2-oleoylamino-1,3-octadecanediol (B) and 2-N-(2-hydroxyhexadecanoyl)amino-1,3-octadecanediol (C) increase the number of keratinocytes which have entered into the S phase, thus indicating stimulation of cell mitotic activity.

EXAMPLE 4

Measurement of the Effect of 2-amino-1,3-octadecanediol and Derivatives Thereof on the Survival of the Hair Follicle in Vitro Viable in vitro hair follicles were prepared according to the technique described in FR-95/08,465, filed Jul. 12, 1995 and assigned to the assignee hereof.

From a scalp biopsy, a rather fine strip of scalp was isolated using a scalpel. The adipose tissue surrounding the follicles was removed with microforceps while avoiding damage to the hair bulb. The follicle was cut and removed with a scalpel under a microscope in order to separate it from its epidermal and dermal surroundings.

The fragment obtained was maintained in culture in Williams E medium, at 37° C., in a humid atmosphere in the presence of $CO_2$.

The survival of the follicles was evaluated each day by counting the living follicles, according to their morphological appearance.

The results are reported as percentage of surviving follicles per day.

The experiment was carried out employing the following compounds at a concentration of 50 nM:

B: 2-amino-1,3-octadecanediol,
C: 2-oleoylamino-1,3-octadecanediol,
D: 2-N-(2-hydroxyhexadecanoyl)amino-1,3-octadecanediol,
in comparison with the culture medium without alkanediol (A).

| Days | 0 | 1 | 5 | 10 | 15 | 20 | 25 |
|---|---|---|---|---|---|---|---|
| A n = 19 | 100 | 100 | 84 | 16 | 0 | 0 | 0 |
| B n = 10 | 100 | 100 | 90 | 20 | 0 | 0 | 0 |
| C n = 9 | 100 | 100 | 100 | 78 | 33 | 0 | 0 |
| D n = 12 | 100 | 100 | 100 | 50 | 42 | 25 | 0 | n = number of follicles tested in the experiment

This experiment evidenced that the alkanediols increased the survival time of the cultured hair follicle.

EXAMPLE 5

Effect of 2-amino-1,3-octadecanediol and Derivatives Thereof on Cell Viability in the Presence of Doxorubicin HaCat cells were cultured as in Example 2.

24 hours after inoculation, the cells were contacted with the various test compounds in a KBM medium (marketed by Clonetics) containing insulin at 5 $\mu$g/ml and hydrocortisone at 0.5 $\mu$g/ml.

The cells were cultured in the presence of the 2-amino-1,3-octadecanediol to be tested until evaluation of cell viability.

Doxorubicin at a concentration of 1 $\mu$g/ml was added to the culture medium for 2 hours at the beginning of the experiment.

Cell viability was evaluated 48 hours later by measuring the mitochondrial respiration. This was carried out using an XTT kit, marketed by Boehringer, according to the supplier's instructions.

The experiment was carried out with the following compounds at a concentration of 50 nM:
C: 2-amino-1,3-octadecanediol,
D: 2-oleoylamino-1,3-octadecanediol,
E: 2-N-(2-hydroxyhexadecanoyl)amino-1,3-octadecanediol,
in comparison with the culture medium without alkanediol and without doxorubicin (A) and with a medium containing only doxorubicin (B).

The results, expressed as percentage, represent the increase in the number of cells with respect to the control (A), namely, with respect to a culture produced under the same conditions in the absence of alkanediol compounds and of doxorubicin.

| A | 0 |
|---|---|
| B | −20 |
| C | +25 |
| D | +28 |
| E | +23 |

Doxorubicin caused a decrease in cell viability. The presence in the culture medium of a 2-amino-1,3-octadecanediol inhibited this effect and increased cell viability.

EXAMPLE 6

Effect of 2-amino-1,3-octadecanediol and Derivatives Thereof on Cell Viability in the Presence of a Compound Based on Sphingenine, N-acetylsphingenine The cells were cultured as in Example 5. N-Acetylsphingenine was at a concentration of 10 $\mu$M.

The experiment was carried out with the following compounds at a concentration of 50 nM:
C: 2-amino-1,3-octadecanediol,
D: 2-oleoylamino-1,3-octadecanediol,
E: 2-N-(2-hydroxyhexadecanoyl)amino-1,3-octadecanediol,
in comparison with the culture medium without alkanediol and without N-acetylsphingenine (A) and with a medium containing only N-acetylsphingenine (B).

The results, expressed as percentage, represent the number of cells with respect to the control (A), namely, with respect to a culture produced under the same conditions in the absence of alkanediol compounds and of N-acetylsphingenine.

| A | 100 |
|---|---|
| B | 57 |
| C | 72 |
| D | 76 |
| E | 78 |

N-Acetylsphingenine caused a decrease in cell viability. The presence in the culture medium of a 2-amino-1,3-octadecanediol tended to counteract this effect.

EXAMPLE 7

This example sets forth specific compositions for topical application to the hair and/or the scalp and can be prepared by simple mixing (A.M.: Active material):

| Rinsable care conditioner: | |
|---|---|
| (a) Rewoquat W75PG* | 2 g A.M. |
| (b) 2-Amino-1,3-octadecanediol | 5 g |
| (c) Mixture of oxyethylenated cetylstearyl and cetyl alcohol | 3 g |
| (d) Preservative, fragrance | |
| (e) Water       q.s. for | 100 g |
| Shampoo: | |
| (a) Sodium lauryl ether sulfate (28% A.M.) | 60 g |
| (b) Cocoylbetaine | 9 g |
| (c) 2-Oleoylamino-1,3-octadecanediol | 4 g |
| (d) Preservative, fragrance | |
| (e) Water       q.s. for | 100 g |
| (f) HCl        q.s. | pH 6 |
| Treatment shampoo: | |
| (a) Sodium lauryl ether sulfate (28% A.M.) | 75 g |
| (b) Empilan CIS** | 1 g |
| (c) 2-N-(2-Hydroxyhexadecanoyl)amino-1,3-octadecanediol | 1 g |
| (d) Water       q.s. for | 100 g |
| Rinsable lotion: | |
| (a) Catinal DC50 ®*** | 0.5 g A.M. |
| (b) 2-N-(2-Hydroxyhexadecanoyl)amino-1,3-octadecanediol | 4 g |
| (c) Preservative, fragrance | |

-continued

| | | |
|---|---|---|
| (d) Water | q.s. for | 100 g |
| (e) NaOH | q.s. | pH 5.5 |
| Aqueous gel: | | |
| (a) Carbopol 940 ®, marketed by Goodrich | | 0.6 g |
| (b) Transcutol ®, marketed by Gattefosse | | 5.0 g |
| (c) Triethanolamine | | 0.3 g |
| (d) Preservatives | | 0.3 g |
| (e) Propylene glycol | | 3.0 g |
| (f) NaOH | | 0.007 g |
| (g) 2-Oleoylamino-1,3-octadecanediol | | 4 g |
| (h) Water | q.s. for | 100 g |
| Lotion: | | |
| (a) 2-Acetylamino-1,3-octadecanediol | | 0.2 g |
| (b) Gantrez es 425**** | | 1 g A.M. |
| (c) Celquat 1200***** | | 0.5 g |
| (d) Ethanol | | 50 g |
| (e) Demineralized water | q.s. for | 100 g |

*1-Methyl-2-tallow-3-tallowamidoethylimidazolium methosulfate/propylene glycol (75/25), marketed by Witco.
**Coconut acid monoisopropanolamide, marketed by Albright and Wilson.
***80% Behenyltrimethylammonium chloride in a water/isopropanol (15/85) mixture, marketed by Toho.
****Monoesterified maleic anhydride/methyl vinyl ether copolymer, marketed by ISP.
*****Copolymer of hydroxyethyl cellulose and of diallyldimethylammonium chloride, marketed by National Starch.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for inducing or stimulating hair growth and/or retarding hair loss on a mammalian subject in need of said treatment comprising topically applying to the hair and/or skin an effective amount of a cosmetic or pharmaceutical composition of matter, comprising a hair growth stimulating and/or hair loss retarding effective amount of at least one 2-amino-1,3-alkanediol compound having the structural formula (I) which compound induces hair growth and/or retards hair loss:

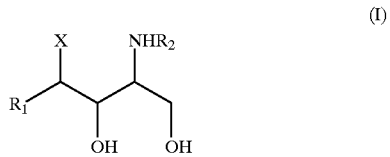

in which $R_1$ is a saturated, and optionally is a hydroxylated, linear or branched hydrocarbon radical having from 4 to 28 carbon atoms; $R_2$ is a hydrogen atom or the radical:

wherein $R_3$ is a saturated or unsaturated, optionally hydroxylated, linear or branched hydrocarbon radical having from 1 to 29 carbon atoms, wherein the hydroxyl group thereof is optionally esterified by a saturated or unsaturated, linear or branched acyl radical having from 2 to 30 carbon atoms; and X is a hydrogen atom or the OH radical, or at least one optical isomer or diastereoisomer thereof, in a physiologically topically acceptable carrier medium therefor.

2. The method of claim 1 where, in the compound of formula (I), $R_1$ is a saturated hydrocarbon radical having from 11 to 23 carbon atoms.

3. The method of claim 1 where, in the compound of formula (I), $R_1$ has 14 carbon atoms.

4. The method of claim 1 where, in the compound of formula (I), $R_1$ is a saturated linear hydrocarbon radical.

5. The method of claim 1 where, in the compound of formula (I), $R_2$ is a radical:

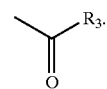

6. The method of claim 5, wherein the $R_3$ group in said compound of formula (I) is a hydrocarbon radical having from 7 to 25 carbon atoms.

7. The method of claim 1 wherein said at least one 2-amino-1,3-alkanediol compound (I) comprises from $10^{-4}\%$ to 20% by weight of said topically administered composition.

8. The method of claim 7 wherein said at least one 2-amino-1,3-alkanediol compound (I) comprises from $10^{-3}\%$ to 10% by weight of said topically administered composition.

9. The method of claim 1 wherein said at least one 2-amino-1,3-alkanediol compound (I) is selected from the group consisting of 2-amino-1,3-octadecanediol, 2-acetylamino-1,3-octadecanediol, 2-octanoylamino-1,3-octadecanediol, 2-tetracosanoylamino-1,3-octadecanediol, 2-N-(2-hydroxyhexadecanoyl)amino-1,3-octadecanediol, 2-oleoylamino-1,3-octadecanediol, 2-hexadecanoylamino-1,3-octadecanediol, 2-N-(2-hydroxydocosanoyl)amino-1,3-octadecanediol, 2-amino-1,3,4-octadecanetriol, 2-hexadecanoylamino-1,3,4-octadecanetriol and 2-N-(2-hydroxyhexadecanoyl)amino-1,3,4-octadecanetriol.

10. The method as defined by claim 9, wherein said at least one 2-amino-1,3-alkanediol compound (I) is 2-N-(2-hydroxyhexadecanoyl)amino-1,3-octadecanediol.

11. The methbd as defined by claim 9, wherein said at least one 2-amino-1,3-alkanediol compound (I) is 2-oleoylamino-1,3-octadecanediol.

12. The method as defined by claim 1, wherein said topically administered composition comprises an effective amount of at least one active agent selected from the group consisting of an antibacterial agent, an agent for combating parasites, an antifungal agent, an antiviral agent, an antiinflammatory agent, an antipruriginous agent, an anaesthetic agent, keratolytic agent, an agent for combating free radicals, a antiseborrhoeic agent, an antidandruff agent, an antiacne agent, an agent which modulates at least one of cutaneous pigmentation, proliferation and differentiation, a substance P antagonist, a calcitonin gene related peptide antagonist, a bradykinin antagonist and nitric oxide synthase inhibitor.

13. The method as defined by claim 12, wherein the topically administered composition further comprises an effective amount of at least one active agent selected from the group consisting of a substance P antagonist, a calcitonin gene related peptide antagonist, a bradykinin antagonists and a nitric oxide synthase inhibitor, in an amount ranging from 0.000001% to 20% by weight thereof.

14. The method as defined by claim 1, wherein the topically administered composition further comprises an agent selected from the group consisting of a hydrophilic or lipophilic gelling agent, a hydrophilic or lipophilic active agent, a preservative, an antioxidant, a solvent, a fragrance, a filler, a sunscreen, an odor absorber and a colorant.

15. The method as defined by claim 1, wherein the topically administered composition further comprises an effective amount of another compound which stimulates hair growth and/or retards hair loss.

16. The method as defined by claim 1, wherein said topically administered composition is selected from the group consisting of a solution, dispersion, lotion, serum, emulsion, milk, suspension, foam, spray, gel, cream, microcapsules, microparticles, an ionic vesicular dispersion and a nonionic vesicular dispersion.

17. The method as defined by claim 1, wherein said topically administered composition is selected from the group consisting of a hair care formulation, shampoo, hair-setting lotion, styling cream or gel, coloring formulation, hair-restructuring lotion, permanent-wave formulation and parasite combatant.

18. The method as defined by claim 1, comprising topically applying said composition to the hair and/or scalp of said mammalian subject, to treat a disorder or affliction associated with hair loss.

19. The method as defined by claim 19, wherein said disorder or affliction is an alopecia induced by chemotherapeutic anticancer therapy.

20. A method for inducing or stimulalting hair growth and/or retarding hair loss on a mammalian subject in need of said treatment comprising topically applying an effective amount of a cosmetic or pharamaceutical composition of matter, consisting essentially of a hair growth stimulating and/or hair loss retarding effective amount of at least one 2-amino-1,3-alkanediol compound having the structural formula (I) which compound induces hair growth and/or retards hair loss:

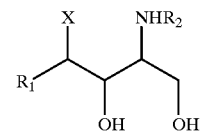 (I)

in which $R_1$ is a saturated, optionally hydroxylated, linear or brached hydrocarbon radical having from 4 to 28 carbon atoms; $R_2$ is a hydrogen atom or the radical:

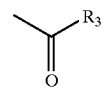

wherein $R_3$ is a saturated or unsaturated, optionally hydroxylated, linear or branched hydrocarbon radical having from 1 to 29 carbon atoms, wherein the hydroxyl group thereof is optionally esterified by a saturated or unsaturated, linear or branched acyl radical having from 2 to 30 carbon atoms; and X is a hydrogen atom or is an OH radical, or at least one optical isomer or diastereoisomer thereof, in a physiologically topically acceptable carrier medium therefor.

21. The method of claim 20 wherein said at least one 2-amino-1,3-alkanediol compound (I) is selected from the group consisting of 2-amino-1,3-octadecanediol, 2-acetylamino-1,3-octadecanediol, 2-octanoylamino-1,3-octadecanediol, 2-tetracosanoylamino-1,3-octadecanediol, 2-N-(2-hydroxyhexadecanoyl)amino-1,3-octadecanediol, 2-oleoylamino-1,3-octadecanediol, 2-hexadecanoylamino-1,3-octadecanediol, 2-N-(2-hydroxydocosanoyl)amino-1,3-octadecanediol, 2-amino-1,3,4-octadecanetriol, 2-hexadecanoylamino-1,3,4-octadecanetriol and 2-N-(2-hydroxyhexadecanoyl)amino-1,3,4-octadecanetriol.

* * * * *